United States Patent [19]

Poss et al.

[11] Patent Number: 5,617,845
[45] Date of Patent: Apr. 8, 1997

[54] INHALATION DEVICE FREE FROM PROPELLENT GAS

[75] Inventors: Gerhard Poss, Schriesheim; Jurgen Wittekind, Frankfurt am Main; Andreas Kuhnel, Oberursel, all of Germany

[73] Assignee: Boehringer Ingelheim KG, Germany

[21] Appl. No.: 237,460

[22] Filed: May 3, 1994

Related U.S. Application Data

[62] Division of Ser. No. 977,450, filed as PCT/EP91/01593 Aug. 30, 1990, abandoned.

[30] Foreign Application Priority Data

Aug. 30, 1990 [DE] Germany .................. 40 27 391.1

[51] Int. Cl.⁶ .................. A61M 15/00; A61M 16/00; B05D 7/14; B65D 83/06
[52] U.S. Cl. .................. 128/203.15; 128/203.12
[58] Field of Search .................. 128/203.12, 203.15, 128/203.21; 604/58; 222/636

[56] References Cited

U.S. PATENT DOCUMENTS

| | | | |
|---|---|---|---|
| 2,587,215 | 2/1952 | Priestly . | |
| 2,829,642 | 4/1958 | De Melfy | 128/203.15 |
| 2,992,645 | 7/1961 | Fowler | 128/203.15 |
| 3,636,949 | 1/1972 | Kropp | 128/200.23 |
| 3,900,138 | 8/1975 | Phillips . | |
| 3,906,950 | 9/1975 | Cocozza | 128/203.15 |
| 3,921,637 | 11/1975 | Bennie et al. . | |
| 4,014,336 | 3/1977 | Mathes . | |
| 4,274,403 | 6/1981 | Struve . | |
| 4,803,978 | 2/1989 | Johnson, IV et al. | 128/200.23 |
| 5,048,514 | 9/1991 | Ramella | 128/203.15 |
| 5,070,870 | 12/1991 | Pearce | 128/203.15 |

FOREIGN PATENT DOCUMENTS

| | | |
|---|---|---|
| 166294A3 | 1/1986 | European Pat. Off. . |
| 0363060 | 4/1990 | European Pat. Off. . |
| 2238505 | 2/1975 | France . |
| 2516387 | 5/1983 | France . |
| 2598918 | 11/1987 | France . |
| 1945257 | 3/1970 | Germany . |
| 2603163 | 8/1976 | Germany . |
| 2749629 | 5/1978 | Germany . |
| 2726934 | 1/1979 | Germany . |
| 3040641 | 5/1982 | Germany . |
| 3535561 | 5/1986 | Germany . |
| 3901963 | 8/1990 | Germany . |
| 2144997 | 3/1985 | United Kingdom . |
| 2165159 | 4/1986 | United Kingdom . |
| WO90/07351 | 7/1990 | WIPO . |

*Primary Examiner*—Kimberly L. Asher
*Attorney, Agent, or Firm*—Sterne, Kessler, Goldstein & Fox P.L.L.C.

[57] ABSTRACT

The invention relates to a propellant-free inhaler which has a storage chamber (6) for a powdered substance to be inhaled, which is associated with a metering device (8), which is manually operated by means of a button, having a metering chamber (7) for receiving a given dose of the powdered substance. The device also has a lateral mouth piece (11) for active breathing in, with an air channel (7) for distributing the particular dose of the powdered substance in the air stream. To ensure that the dosage provided is highly reproducible, a high proportion of this dose leaves the inhaler and the medicinal substance is reproducibly dispersed, a trigger operated pump (12,19,20) is provided which can be manually primed before the inhalation process by means of a button (1,42) and which can be actuated in synchronism with the breathing, thereby generating a current of foreign air which disperses the metered substance.

10 Claims, 10 Drawing Sheets

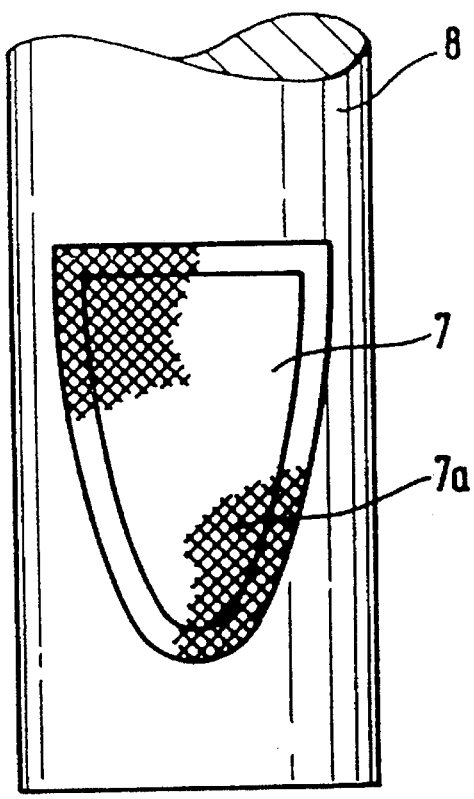
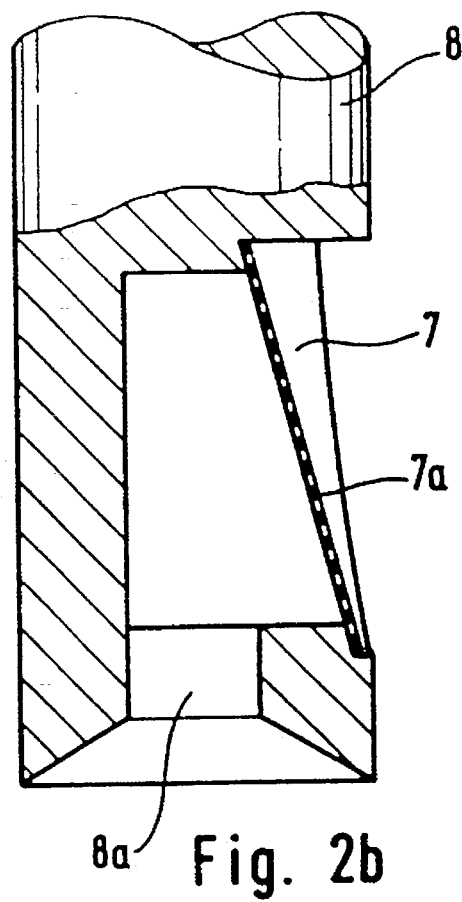
Fig. 2a    Fig. 2b
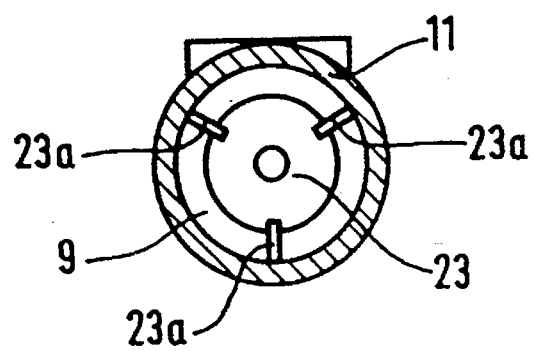
Fig. 3

INHALATION DEVICE FREE FROM PROPELLENT GAS

This application is a division of application Ser. No. 07/977,450, filed as PCT/EP91/01593 Aug. 30, 1990, now abandoned.

FIELD OF THE INVENTION

The invention relates to a propellant-free inhaler having a storage chamber for a powdered medicinal substance to be inhaled and associated therewith a manually operable metering device for receiving a given dose of the medicinal substance for the particular inhalation process in at least one metering chamber, and with a lateral mouth piece for actively breathing in, which has an air channel for distributing the particular dose of medicinal substance in the air stream.

RELATED ART

An inhaler of this kind is known from DE 35 35 561 A1.

In this known inhaler, underneath the storage container and parallel to the mouth piece is a charging valve which has recesses (metering chambers) for measuring out the medicinal substance. When the recesses are turned towards the storage container they are automatically filled. If, as a result of a 180° rotation of the charging valve, the filled recess is turned towards the air chamber of the mouth piece, the dose of powder falls out of the recess into a cavity in the air channel, as a result of gravity, aided by a jogging mechanism, and from there is inhaled into the patient's lungs by active breathing in. The air channel has a constricted area which is intended to promote the mixing of the air with the medicinal substance by turbulence, ie. forming an aerosol.

Thus, in this device, the aerosol is produced by active breathing in, in such a way that the air breathed in by the user is passed over the powder and picks it up as it goes along.

The known inhaler has two serious disadvantages. On the one hand the dose to be inhaled is not sufficiently reproducible. On the other hand the air stream which is produced by actively breathing in is incapable of bringing the entire dose out of the device and dispersing the medicinal substance in the air stream, in spite of the assisting action of the constriction in the air channel. It should be taken into account that, depending on the type of powder to be inhaled, it should typically have a particle size of only about 5 µm in order to reach the site of action in the bronchial tubes. However, powders with such a fine particle size have a tendency to clump together on storage, so that when the inhaler is used and the powder is not thoroughly broken up, as is the case when it is simply breathed in, at least some of the powder is inhaled in the form of clumps with a larger diameter than that of the primary particles. These clumps do not arrive at the site of activity in the bronchial tubes, with the result that there is a considerable metering error which is unacceptable when powerful drugs are being administered.

SUMMARY OF THE INVENTION

The aim of the invention, starting from the propellant-free inhaler described hereinbefore, is to construct this inhaler in such a way that the dose provided is highly reproducible, a high proportion of this dose leaves the inhaler and the medicinal substance is reproducibly dispersed.

The solution to this problem is achieved according to the invention by providing a trigger-operated pumping arrangement associated with the metering chamber, having a manually activated tensioning device and mechanical switching means which respond to the low pressure produced by breathing in and actuate the tensioning device, thereby producing a foreign air current which blows out the filled metering chamber, dispersing the substance.

The inhaler according to the invention operates with a metered, automatically triggered foreign air current which is synchronous with the breathing. The blast of compressed air blows the given dose of the medicinal substance to be inhaled right out of the metering chamber into the air channel. The dose is therefore constant to a high degree from one inhalation process to the next. The blast of compressed air causes it to be very finely divided, thereby considerably reinforcing the inhaling action. If there are clumps of powder present, these are broken up by the pulse of foreign air.

In order to avoid the disadvantage of insufficient dispersal, devices are known in which the clumps of powder are broken up by means of a pulse of foreign air. A device of this kind is disclosed, for example, in WO-A-9007351. In order to generate this pulse of foreign air, a volume of air compressed by a piston or bellows is released very rapidly. The pulse of air picks the powder up and the turbulences and shear force it produces break up any clumps and return them to the primary particles. The dispersed product can then penetrate deeply into the bronchial tubes, thanks to its renewed fineness, without any appreciable loss of substance in the oral or pharyngeal cavities.

However, when producing an aerosol in the manner described, it is necessary to release the foreign air pulse at the precise moment of maximum breath flow whilst breathing in. If it is not triggered at this moment, this results in defective operation and incorrect dosing. This release of the foreign air pulse in synchronism with the breathing is achieved by the mechanical switching means which respond to the low pressure caused by breathing.

The production of a foreign air current in inhalers is known per se from U.S. Pat. No. 3 921 637. In the known inhaler, a manually operated bellows pump is provided which generates air at increased pressure only as long as pressure is exerted on the pump bellows by hand. In the known device, between the pump and a chamber in which the dose to be inhaled is accommodated in the form of capsules, a valve arrangement is provided which is operated by switching means which respond to the breath flow during breathing in. By contrast with the invention, therefore, these switching means do not actuate the trigger mechanism of a tensioned pump but open a valve. The switching means consist of a flap balanced out by springs, which opens the valve by means of levers.

According to an advantageous embodiment of the invention, behind tile metering chamber is a dispersing nozzle through which the foreign air current is passed. This nozzle ensures particularly good dispersal and, if necessary disaggregation of the medicinal substance in the breath flow.

In one embodiment of the invention, the element for manual operation of the metering device is mechanically coupled to the activation of the tensioning device. Because of this arrangement, the device according to the invention can be primed by a single tensioning movement for the dosing and the breath triggering.

Another embodiment of the invention is characterised in that the pumping arrangement has a pumping chamber with an air outlet connector and a pump piston which can be tensioned by manual actuation counter to the force of a spring and can be releasably latched on the side of the pump chamber which is remote from the air outlet connector. A tensionable piston pump of this kind is a particularly simple but highly effective embodiment of a trigger-operated pumping arrangement for the device according to the invention. Tensionable piston pumps are also known per se in medical equipment (DE- 27 26 934 A1). However, they cannot be triggered automatically and in synchronism with the breathing.

Other characteristic features and advantages of the invention will become apparent from the description of embodiments by way of example illustrated in the drawings.

BRIEF DESCRIPTION OF THE DRAWINGS

FIG. 2a shows a view parallel to a horizontal axis of the embodiment of the metering chamber shown in FIG. 1, and FIG. 2b shows a cross-sectional view of the embodiment of the metering chamber shown in FIG. 1.

FIG. 3 is a cross-sectional view of the suspension of the nozzle shown in FIG. 1 in the air channel of the mouth piece, FIG. 5 shows the embodiment according to FIG. 1 immediately after the dose blown out has been breathed in.

DESCRIPTION OF THE PREFERRED EMBODIMENTS

Figure 1:
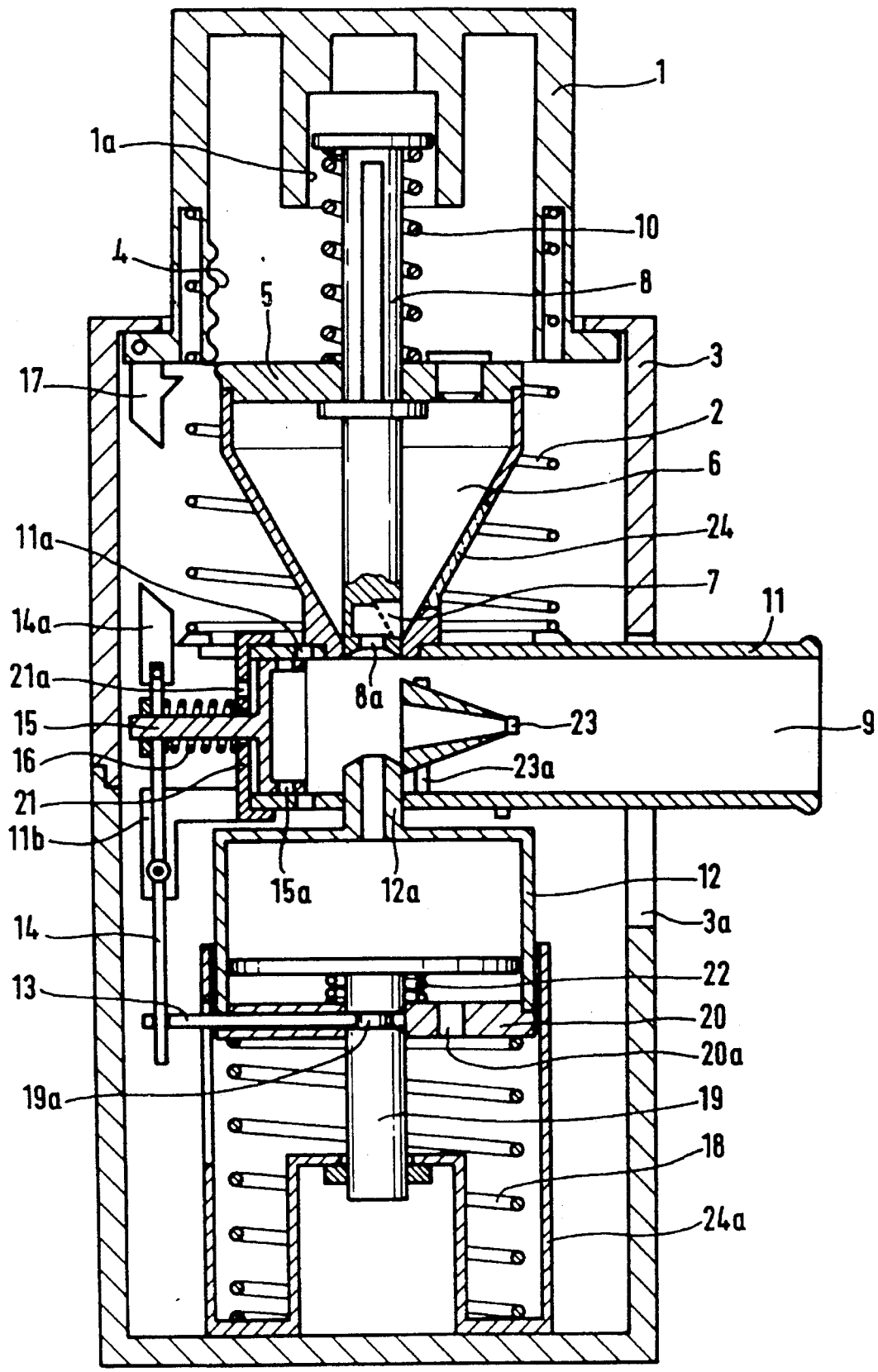
FIG. 1 is an embodiment of the propellant-free inhaler according to the invention in its normal condition, shown in section.

The propellant-free inhaler shown in FIG. 1 has a housing 3 with a lateral opening 3a in which, at the top, a push button 1 is mounted so as to be movable counter to the force of a spring 2 which is supported on the housing. The push button 1 has, on the inside, toothed or corrugated edges 4 and also has a lever 17 formed thereon for latching with a counter part on the housing 3 on which the spring 2 also rests. The inhaler also has a funnel shaped storage container 6 as a supply chamber for the powdered medicinal substance which is to be inhaled. This storage container can be closed off by means of a lid 5 and has a window 24 showing how much of the substance is left. Associated with the storage container is a metering punch 8 which has a metering chamber 7 for receiving the dose of medicinal substance to be breathed in at each inhalation. This metering chamber is shown in more detail in various views in FIGS. 2a and 2b. FIG. 2a—a view parallel to a horizontal axis—shows that the metering chamber is substantially triangular in cross-section. As can be seen particularly from the cross-sectional view in FIG. 2b, it has an undercut on which is mounted a perforated base 7a which bounds the metering chamber to the inside.

The metering punch 8 passes through the lid 5 and the end of the storage container 6 nearest the cone and is movably mounted therein, counter to the force of a spring 10 which rests on the other side in a recess 1a in the push button 1. At the metering chamber end, the metering punch has a bore 8a for the supply of air to the metering chamber 7 and at this end it is suitably shaped for interlocking attachment to a connector 12a of a pump housing 12, which will be described more fully hereinafter.

The lid 5 of the storage chamber has a rounded edge which the corrugated edge 4 of the inner wall of the push button brushes past when the push button 1 is depressed, thereby jogging the storage container 6. In this way the metering chamber 7 is uniformly filled by means of the metering punch 8.

The inhaler also has a laterally mounted mouth piece 11 for actively breathing in with an air channel 9. A nozzle 23 is mounted in this air channel via bars 23a (see FIG. 3). The mouth piece 11 is fixedly connected to the storage container 6 and to the connector 12a of the pump housing and forms a movable unit therewith. At the left hand end it is closed off by a lid 21 which has an air escape bore 21a. At this end nearest the lid the mouth piece 11 also has ventilation bores 11a, the function of which will be explained more fully.

The inhaler also has a pump arrangement for generating a jet of compressed air (foreign air current) during the inhalation process. This pump arrangement has the pump housing 12 already mentioned, with the connector 12a out of which the air is expelled. The pump housing is closed off by a base 20 with an air escape bore 20a; a releasing tongue 13 is mounted in radially movable manner in this escape base. The pump arrangement also has a pump piston 19 which is movably mounted in the pump base counter to the force of a spring 22. The pump piston 19 has an encircling groove 19a into which the releasing tongue 13 engages in the tensioned state of the spring 22 and holds the pump piston in the tensioned state. The pump piston 19 is also mounted in a housing insert 24a which receives a spring 18 supported on the other end of the pump housing base 20.

In order to initiate the pumping movement a trigger mechanism is provided which, in the embodiment shown, responds automatically when the patient actively breathes in. This trigger mechanism has a trigger piston 15 which is held counter to the bias of a relatively weak spring 16 in the mouth piece 11. Ventilation bores 15a are provided on an extension of the trigger piston. Another component of the trigger mechanism is the releasing lever 14 which is rotatably mounted on a projection 11b of the mouth piece 11. This releasing lever 14 is movably guided in the piston rod of trigger piston 15 and has, at its top end, a releasing element 14a for the push button latching lever 17. On the other side it is movably guided in the releasing tongue 13, which is also part of the trigger mechanism.

FIG. 1 shows the inhaler in its normal operative condition, ie. in the condition before use. The spring 22 of the pump piston 19 is tensioned; the other springs 2,10,16 and 18 are in the relaxed state.

Figure 4:
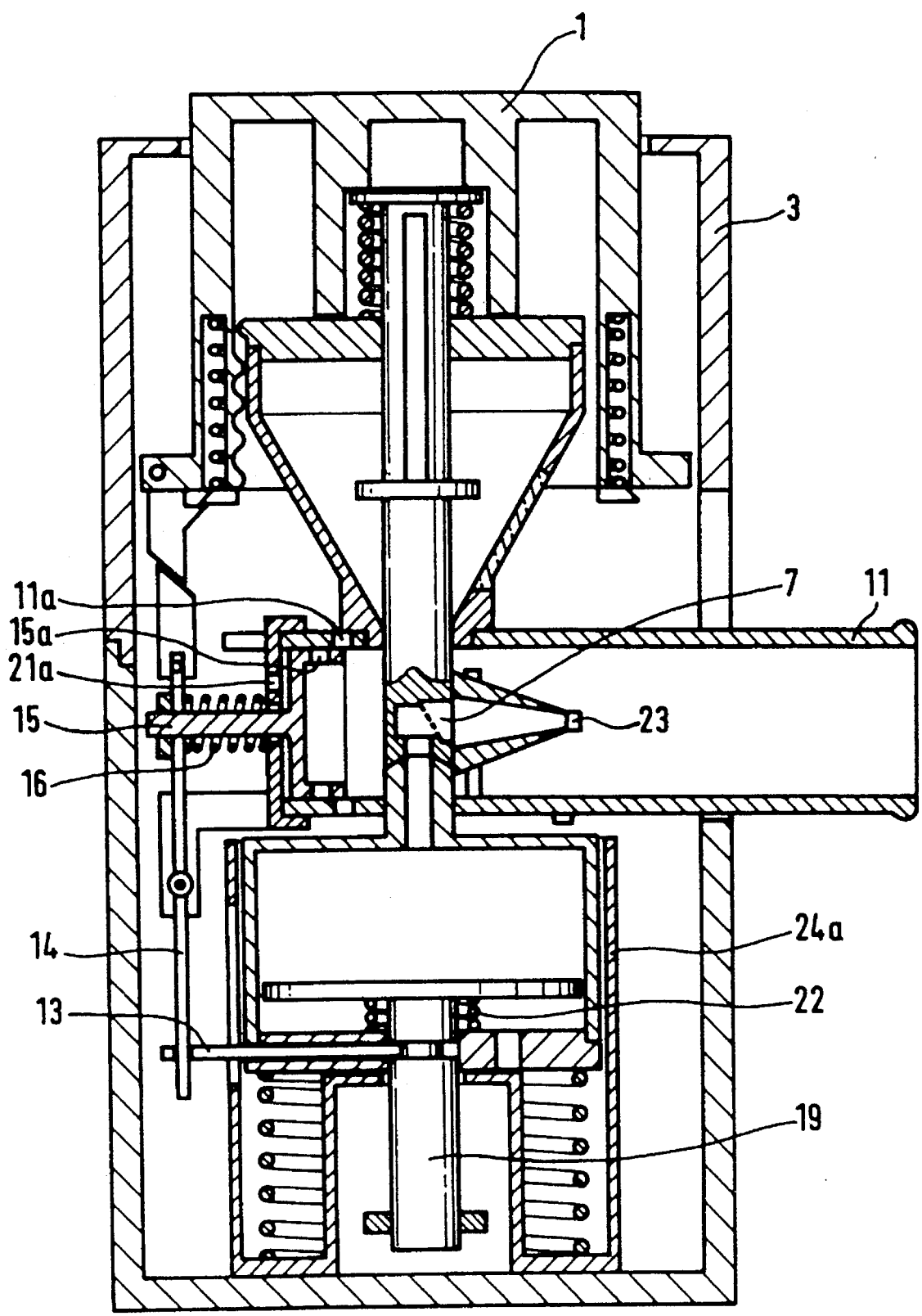
FIG. 4 shows the embodiment according to FIG. 1 in the position ready for inhaling.

In order to achieve the condition ready for use the following manoeuvres have to be carried out:

the push button 1 is depressed manually counter to the force of the spring 2. During this procedure the toothed or corrugated edge 4 is brushed past the container lid 5 and in this way the powder storage container 6 is jogged and the metering chamber 7 is filled. As this push button 1 continues to be depressed counter to the force of the spring 10, the metering punch 8 is pressed down until it abuts on the pump connector 12*a*. The spring 10 is put under tension. As the push button 1 is subsequently depressed fully, the entire movable unit consisting of the powder storage container 6, mouth piece 11, pump housing 12, trigger mechanism 13,14, 15,16 is moved into the lowest position, whilst the push button is locked on the housing by means of its moulded-on lever 17. As it is depressed fully, the spring 18 is put under tension and the pump piston 19 together with the releasing tongue 13 located in the pump housing base 20 is also moved downwards. The inhaler is now in a state of reandiness, ie ready for inhaling. This state of readiness is illustrated in FIG. 4. The metering chamber 7 is now directly level with the nozzle 23. All the springs, with the exception of the return spring 16 associated with the trigger piston 15, are tensioned. During inhalation, the active breathing in causes a drop in pressure in front of the trigger piston 15 in the mouth piece 11. The trigger piston 15 is moved forwards counter to the weak spring 16 and actuates the pump piston 19 by means of the releasing lever 14 and the releasing tongue 13. The air escape bore 21*a* in the mouth piece lid 21 prevents an low pressure from occurring on the rear of the trigger pistol.

Figure 5:
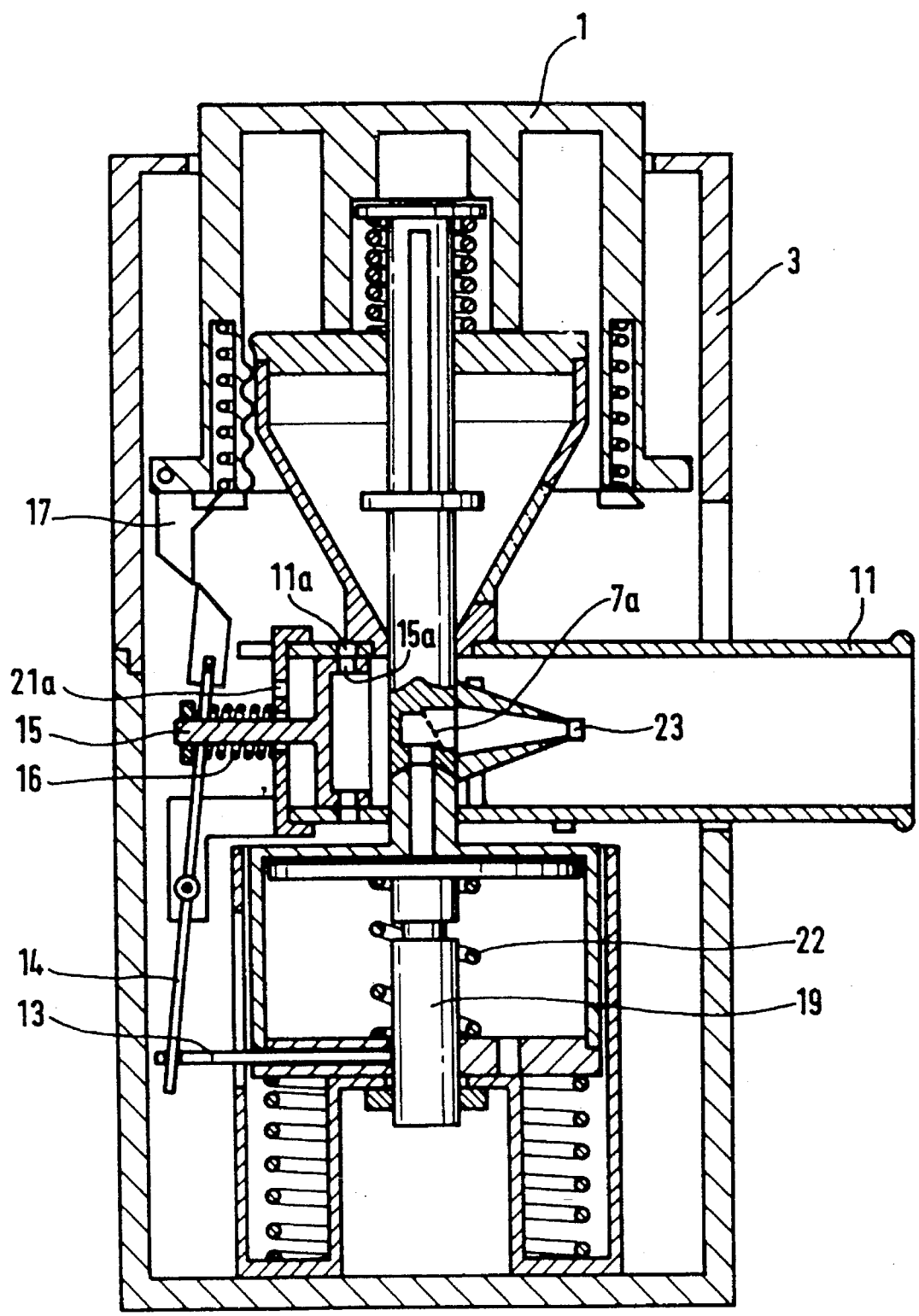

The released pump piston 19 is jerked upwards by the spring 22. The volume of air delivered by the pump piston is pressed through the perforated base of the metering chamber 7 in a jet. The jet of air blows the powder on the screen through the nozzle 23 and thereby disperses it. As the active inhalation continues, foreign air can flow through the bores 11*a* in the mouth piece wall and 15*a* in the trigger piston 15, which register during the suction process, so that the dispersed powder is mixed with the main breath flow in the mouth piece. This operational state immediately after the use of the inhaler is illustrated in FIG. 5.

After the inhalation process has ended, the trigger piston 15 automatically returns to its starting position by release of the return spring 16. The push button 1 is released by the lever 14 via the latching lever 17 and returns to its initial position shown in FIG. 1 as a result of the tension of the springs 2,10 and 18 and whilst tensioning the spring 22, The elements of the inhaler shown in FIGS. 1 to 5 are embodiments; the invention is, however, not restricted to them. As a possible alternative to the trigger mechanism shown in these drawings, the trigger piston 15 may be replaced by a flap and the lever mechanism 14 by a bent lever construction.

In another alternative embodiment, the pump unit consisting of the components 12,18,19 and 22 may also be mounted above the mouth piece 11. It is also possible to use a tensionable bellows as the pumping unit.

The construction of the inhaler may, in theory, also be designed so that the pump piston 19, ie. the spring 22, is not put under tension until the push button 1 is actuated.

The embodiment according to FIG. 1 is directed to automatic actuation of the pump by a trigger mechanism as the patient breathes in. Theoretically, this trigger mechanism may also be replaced by a manually operated release button.

It is possible to refill the device. For this purpose, the assembly consisting of the powder storage container 6, metering punch 8 and spring 10 can be replaced. Either the push button 1 has to be removed or the upper part of the device should be removable by unscrewing. Alternatively, the lid 5 of the powder storage container 6 may be constructed in such a way, eg. equipped with a closure stopper, that powder can be added from a refill cartridge.

The filling of the metering chamber 7 at the end of a funnel shaped storage container is also one of a number of possible alternatives. A preferred variant will now be described more fully with reference to FIGS. 6 to 10.

It is not possible to meter poorly flowing powder (eg. fine grained glucose) by filling a metering volume without taking active additional measures, eg. vibrating the storage container. The method of metering about to be described, which is hereinafter referred to as "strip-pull metering", makes it possible to achieve an even better filling of the metering chamber for powder which does not readily flow, and hence better reproducibility of the dose prepared.

Although the strip-pull metering can be advantageously used precisely with the inhaler according to the invention, it can in principle also be used with other inhalers.

Figure 6:
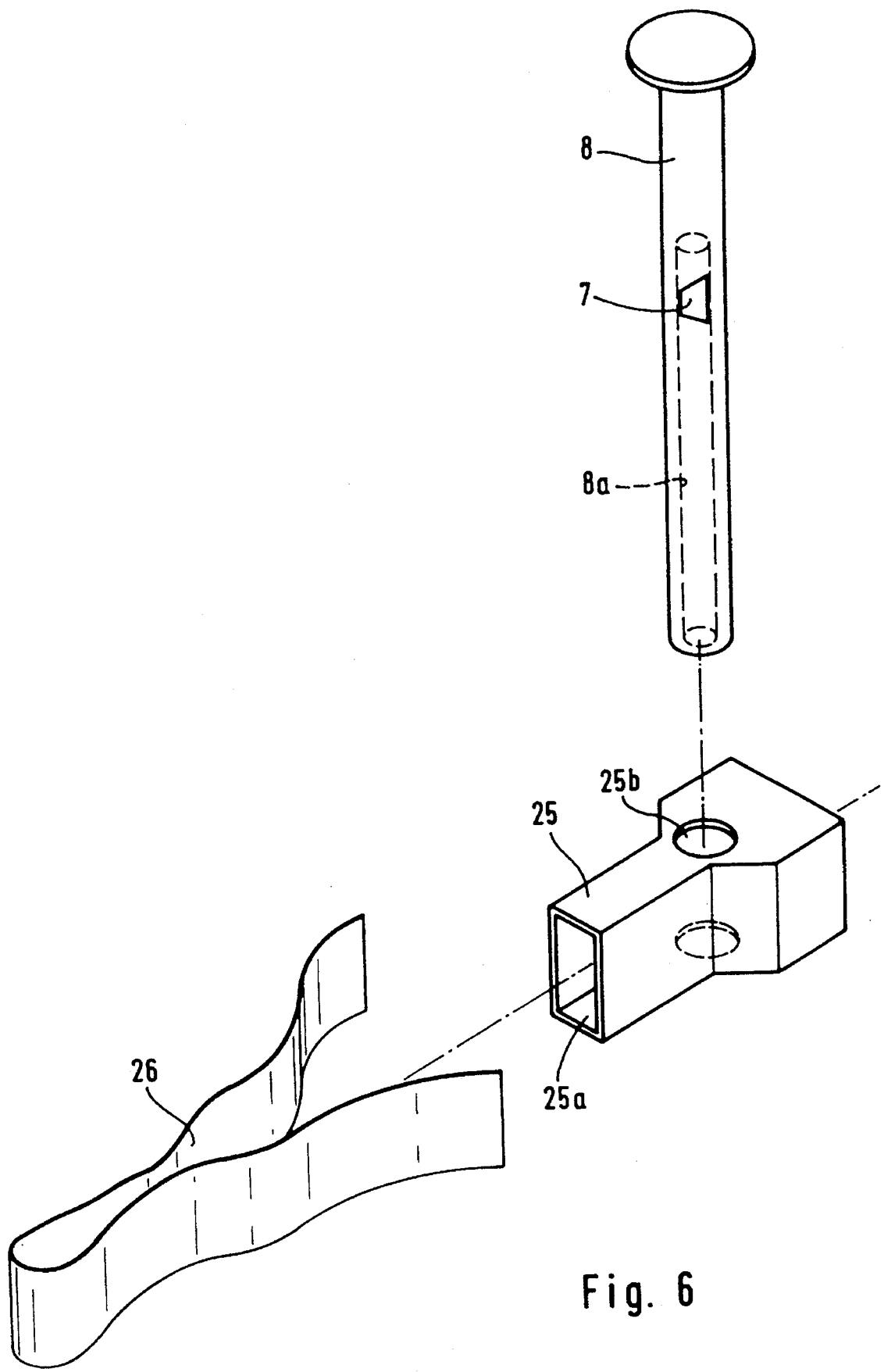
FIG. 6 is an exploded view of a particular arrangement for metering the active substance to be inhaled (strip-pull metering)
Figure 7:
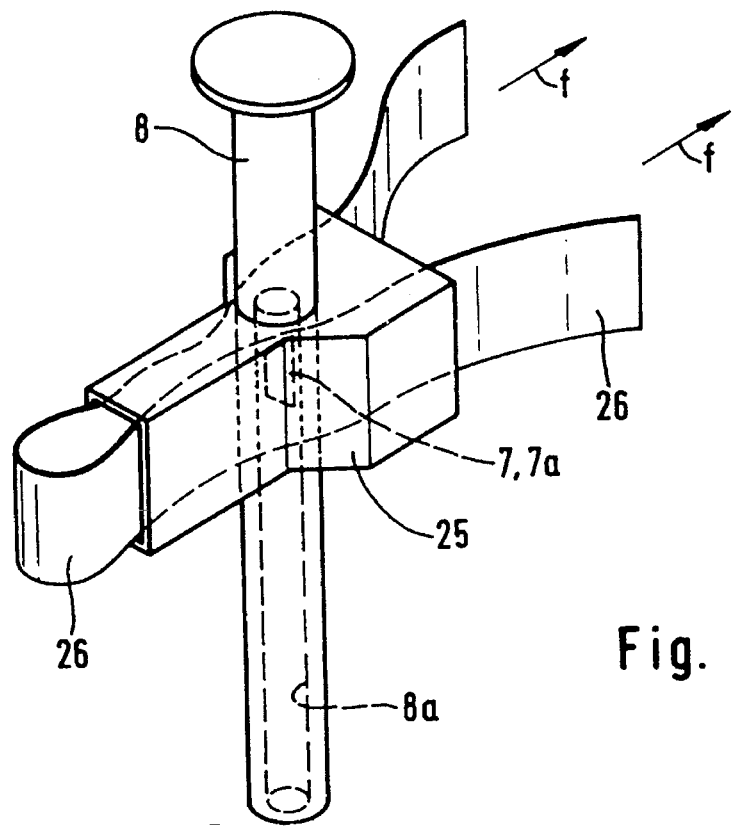
FIG. 7 is the metering arrangement according to FIG. 6 in the installed condition, in a position which enables the storage container to be filled.
Figure 8:
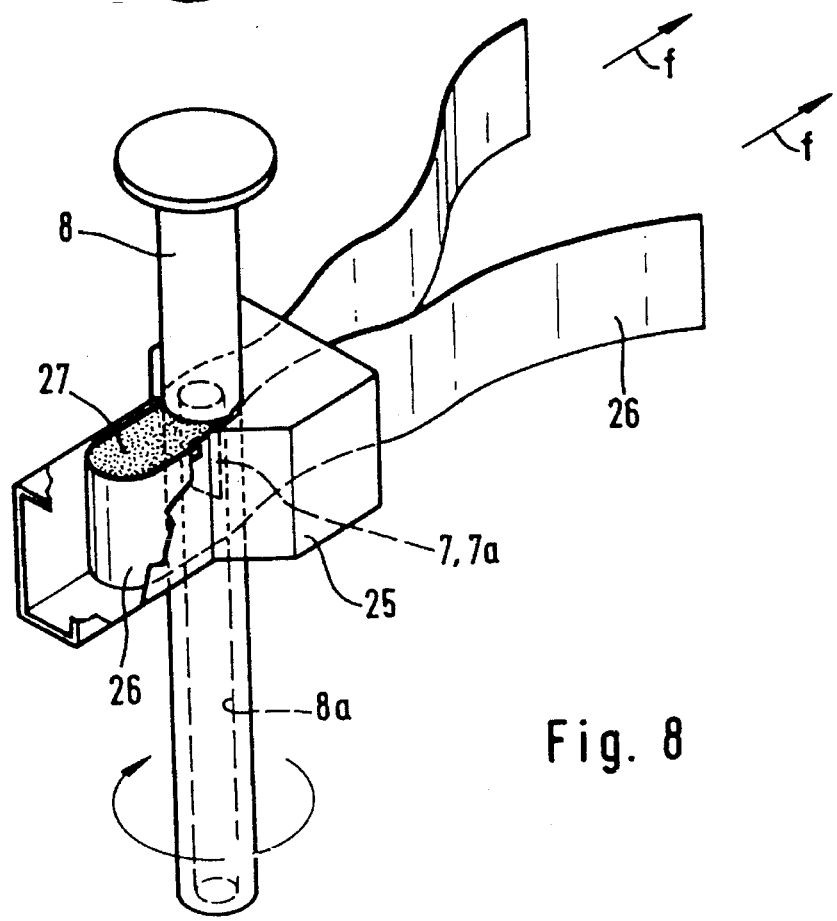
FIG. 8 shows the metering arrangement according to FIG. 6 in a position in which the metering chamber is being filled by rotation of the metering punch.
Figure 10:
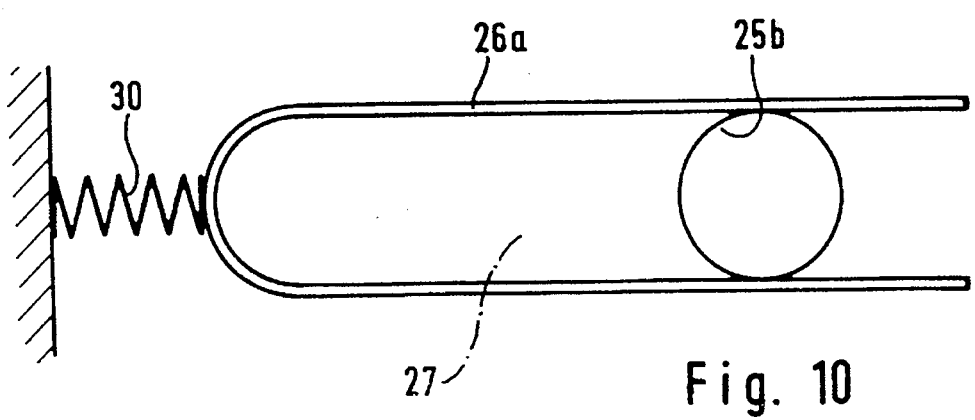
FIG. 10 is a schematic view of an alternative embodiment of the metering arrangement according to FIG. 6.

FIG. 6 shows an exploded view of the important components of strip-pull metering, namely a magazine 25 (which replaces the storage container 6 in FIG. 1, for example), a strip 26, the metering punch 8 with the metering chamber 7 and then axial bore 8*a* which extends from the foot of the metering punch to the metering chamber 7. The metering punch is received in the opening 25*b* of the magazine 25, as can be seen in FIG. 7. The strip 26 is looped in by its free ends at the narrow end face of the magazine 25; these free ends pass through the magazine and emerge at the opposite end face. The charge 27 of powder contained in the magazine 25 is surrounded at the back and on the sides by the looped strip during operation, as shown in FIG. 10, and is subjected to an advance "f" towards the metering punch 8 or metering chamber 7 along the longitudinal axis of the magazine. The strip consists of a strip of paper of sufficient tensile and tear strength, preferably silliconised or TEFLON-coated (synthetic fluorocarbon resin, E.I. du Pont de Nemours & Co.) on both sides, with a defined surface roughness. This is intended to reduce the adhesion of the powder to the strip and minimise the friction between the walls of the magazine, the paper and the metering punch.

The magazine may be filled at the back in a position of the strip corresponding to FIG. 7; the charge of powder is then compressed slightly against the metering punch by pulling the loop of strip.

Metering is carried out by means of a specially shaped metering notch 7 as a metering chamber in the metering punch 8, which is rotated past the slightly compressed powder charge 27 (FIG. 8) in a given direction of advance, in accordance with the geometry of the notch (in the clockwise direction) and thus filled. According to another embodiment the metering punch 8 performs a lifting movement. In this embodiment the metering notch is preferably inclined by 45° to the longitudinal axis of the metering punch. The metering notch is backed at the rear, towards the axial bore 8*a*, with a fine stainless steel perforated mesh 7*a*, for example similar to the arrangement in FIG. 2*b*. The mesh size is preferably about 5–300 μm, preferably about 50 μm.

There are several possible ways of removing the dose from the motoring notch 7. One of these, which is based on the embodiment shown in FIG. 1, is illustrated in FIG. 9.

After the motoring notch 7 has been filled by the rotary or lifting movement as described, the metering punch 8 is pressed down through the bores 25b of the magazine 25—analogously to the transition from the operational state in FIG. 1 to that shown in FIG. 4—until the metering notch 7 is positioned in a small, specially formed dispersing volume 28 (not shown in detail) in front of a specially formed die 29 (again not described in detail). The process of shaving off the powder as the metering punch is pushed through the bores 25b of the magazine makes the dosing even more precise.

Figure 9:
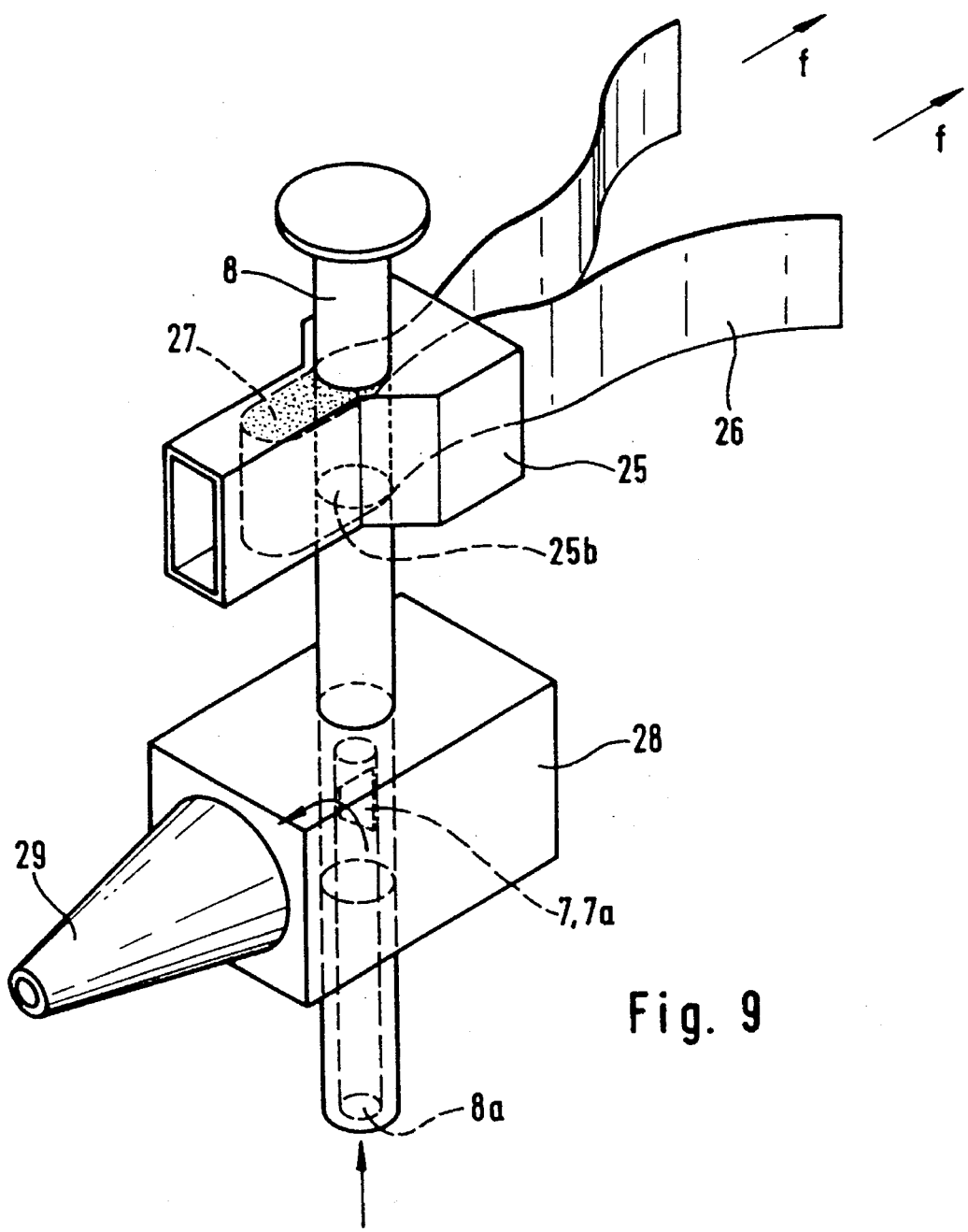
FIG. 9 shows the metering arrangement according to FIG. 6 in a position in which the medicinal substance contained in the metering chamber is expelled.

In the position shown in FIG. 9, a jet of compressed air is directed through the bore 8a onto the base of the metering notch, the perforated mesh 7a, in order to blow out the powder contained in the notch on the perforated mesh. This jet of compressed air may be produced, for example, by a pump arrangement according to FIG. 1; other embodiments are also possible.

The three volumes of the front (narrow end) and back (wide end) of the magazine can be filled with desiccant in order to protect the powder from the effects of moisture.

To ensure more accurate metering of the active substance it may also be mixed with a carrier.

An important feature of the strip-pull metering system is that the wall of the slowly emptying magazine is moved along in the direction of conveying together with the powder charge as the metering notch is filled. The strip 26 may, in theory, also be replaced by a rigid wall, eg. a U-shaped bracket 26a (FIG. 10), which is under gentle pressure from a spring 30 and comes after the storage space.

If the strip-pull metering system is used within the framework of an embodiment according to FIG. 1, the linear movement of the push button 1 is converted into a rotary movement for the metering punch 8.

Figure 11:
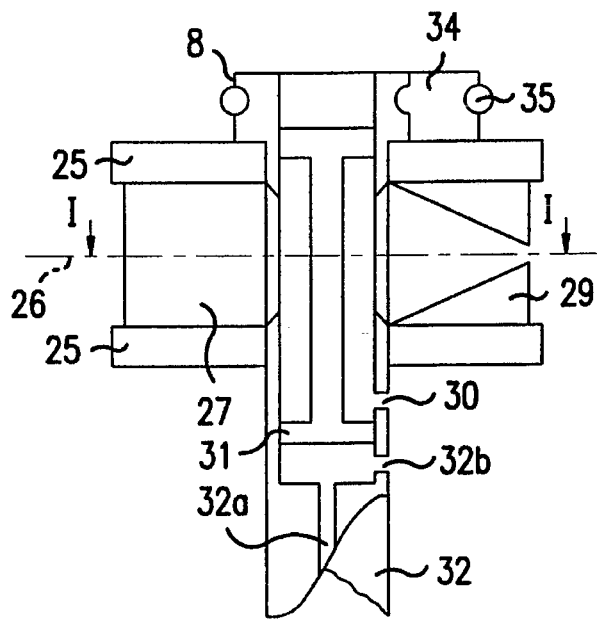
FIGS. 11–13 show a further embodiment of a strip-pull metering in three different views.
Figure 12:
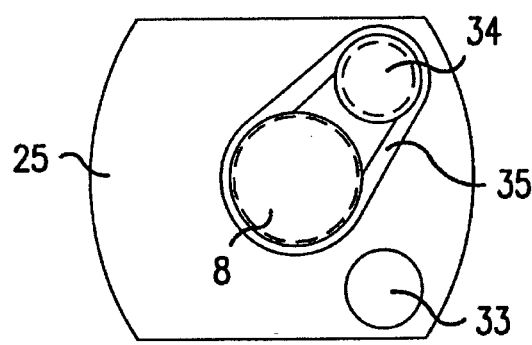
Figure 13:
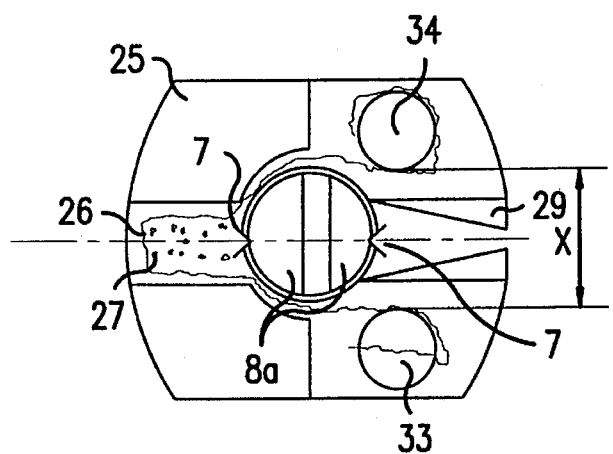

FIGS. 11–13 show another, preferred embodiment of strip-pull metering. This embodiment is even more refined in construction compared with the basic representations in FIGS. 7–9. It is an integral component of the other embodiment, shown in the following FIGS. 14 and 15, of the inhaler according to the invention, which is the preferred embodiment, compared with the embodiment shown in FIGS. 1–5.

In order to emphasise the main common features of the embodiments by way of example, elements of similar function have been given the same reference numeral, even if they are not completely identical in construction.

FIGS. 11–13 show a housing, in the form of a double disc, for the magazine 25 of the strip-pull metering system, the spacing between the two discs corresponding to the width of the strip 26.

FIG. 11 shows a longitudinal section through this magazine, FIG. 12 shows a plan view of the magazine according to FIG. 11 and FIG. 13 shows a section along the line I in FIG. 11.

The strip 26 looped into the magazine comprises the powder supply, the powder charge 27 (FIG. 13) which is bounded on the right hand side by the metering punch, a metering pin 8. The metering pin 8 passes rotatably through the magazine 25 and, in this embodiment, has two metering notches 7. It is also possible to have embodiments with more than 2 metering notches distributed over the metering circumference. The metering notches are expediently closed off at the back by a sintered plastics, glass, metal, net or a screen. The metering pin 8 also has a number of chambers 8a corresponding to the number of metering notches, such that only the metering notch which is to be "blown out" can be acted upon, via the associated chamber, more particularly with the dispersing jet of compressed air from a trigger-operated pump. The two chambers, separated by walls 31, are diagrammatically shown in FIG. 11, whilst the opening 30 constitutes the inlet for the dispersing air. In the lower part of the metering pin 8 is a coupling member 32 by means of which the metering pin can be connected to a rotary drive. This section of the metering pin has a bore 32b for a low pressure channel and a longitudinal bore 32a for transmitting the low pressure, the significance of which will be explained more fully in connection with FIGS. 14 and 15.

The dispersing nozzle 29 is connected to the metering notch 7 to be blown out or the associated chamber in the metering pin 8. The nozzle is preferably mounted in the magazine by means of a suitable device (not shown), eg. a cam, in such a way that the nozzle easily lifts away from the metering pin during transporting of the strip and hence during rotation of the metering pin 8 in the region of entry of the metering notch 7 into the metering area, in order to avoid any powder being scraped off.

The advance of the strip is of particular importance to the operational reliability of the strip-pull metering system. The embodiment shown by way of example is FIGS. 11–13 envisages an equally favourable constructional solution. It discloses a pin 33 to which is attached one end of the strip. The other end of the strip is secured so that it can be wound on the strip tensioning pin 34. The strip tensioning pin 34, the winding spindle, is coupled to the metering pin 8 via a belt 35. Instead of the belt drive it is also possible to use a toothed wheel drive or the like. By rotating the metering pin 8 the belt tensioning pin 34 is driven by the belt 35. The strip 26 iS thus put under tension and compresses the supply of powder 27 until a certain strip tension is produced. When this strip tension is produced the belt slips through, in the manner of a slipping clutch, on the strip tensioning pin 34. During this operation the metering notch 7 is filled.

It is important that the force with which the loop presses the slightly compacted powder charge 27 against the metering pin 8 is limited and that the powder is only subjected to pressure at the moment of metering. This prevents wedging of the powder supply 27 or the associated part of the strip in the magazine 25.

Another particular construction feature is the size of the loop of strip on the metering pin 8. The looping round the metering pin is expediently selected so as to go beyond the (perpendicular) diameter of the metering pin (FIG. 13), ie. the looping angle is greater than 100°. This is achieved by making the dimension X, the free inner space between the pins 33 and 34, less than the external diameter of the metering pin 8. This measure largely prevents soiling of the punch and ensures that the metering notch is filled cleanly.

One major advantage of the strip-pull metering system is that it is independent of position.

Figure 14:
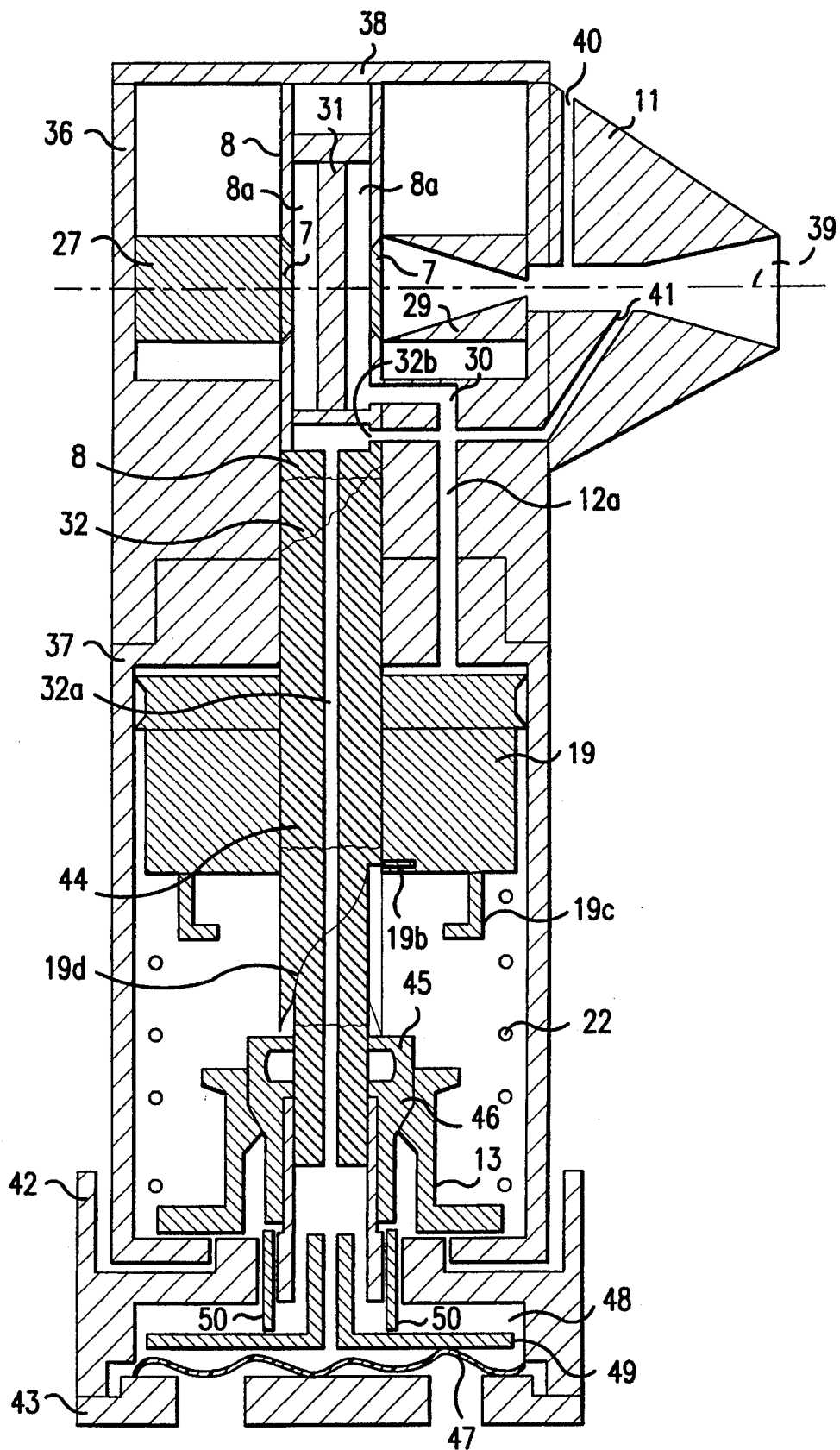
FIG. 14 is another embodiment of the propellant-free inhaler according to the invention in the normal state in a sectional diagrammatic view.
Figure 15:
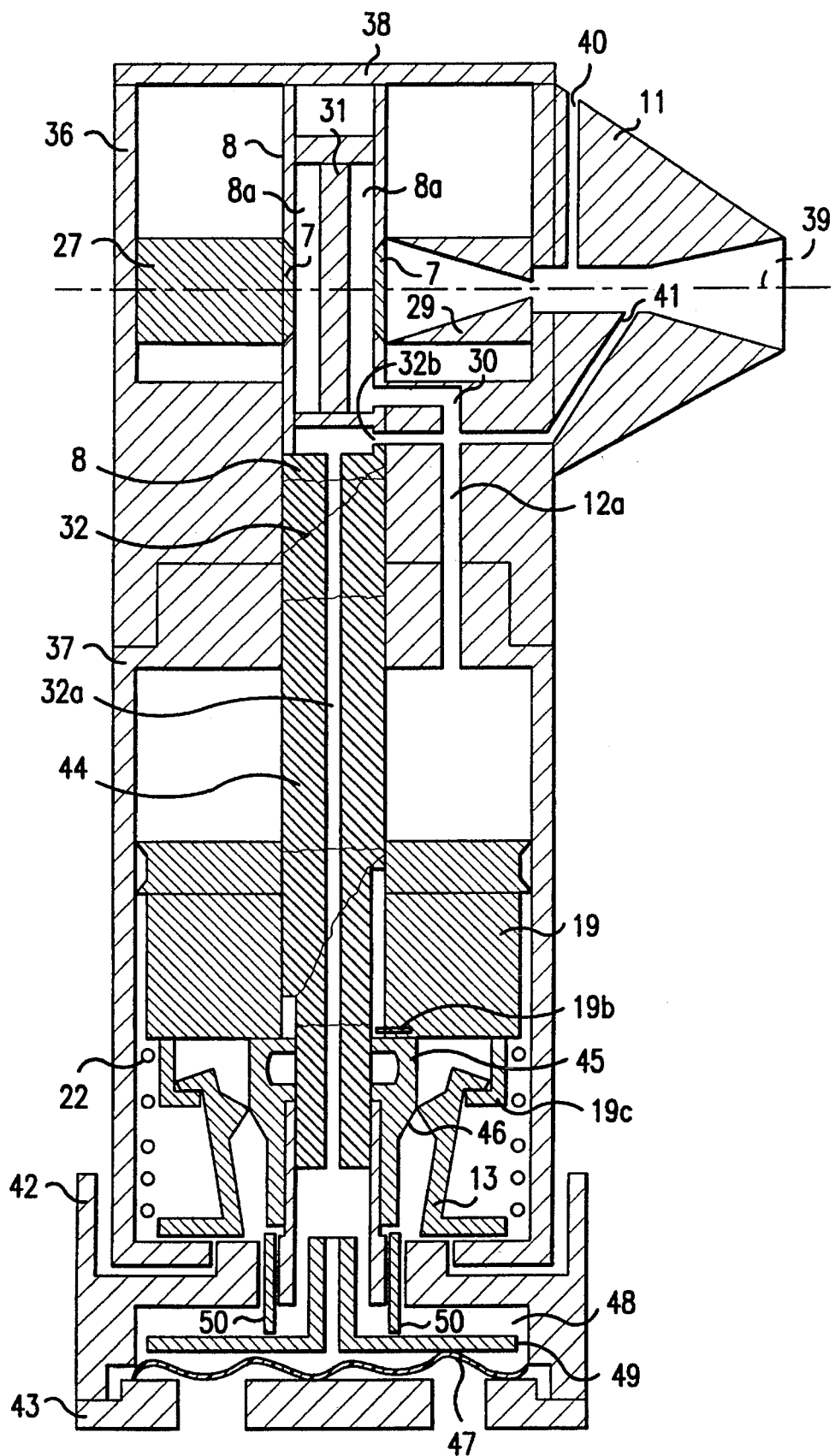
FIG. 15 is the embodiment according to the FIG. 14 in the position ready for inhaling.

FIGS. 14 and 15 show another embodiment of the inhaler according to the invention in which a strip-pull metering system according to FIGS. 11 to 13 is provided.

This inhaler has a two-part housing, namely the top housing 36, which is closed off at the top by a lid 38, and the pump housing 37 which simultaneously forms the cylinder for the piston 19 of the pumping arrangement. Both housing parts are preferably made of plastics and have conventional connecting members (not shown), eg. a screw connection.

The top housing 36 accommodates the strip-pull metering system according to FIGS. 11 to 13 which need not be explained further at this point. The mouth piece 11 which is located opposite the dispersing nozzle 29 of the strip-pull metering system is also mounted on the top housing. The mouth piece 11 has an air chamber in the form of an inhaling nozzle 39 and breathing bores 40 for the flow of external air during inhalation. The mouth piece 11 also has a low pressure channel 41 which communicates with the bore 32b on the metering pin 8 (FIG. 11) and hence with the longitudinal bore 32a. During active breathing in, the acceleration which the air in the nozzle undergoes produces a low pressure in the nozzle and hence in the channel 41, and this low pressure continues into the longitudinal bore 32a. The low pressure channel is therefore expediently provided at that point in the nozzle where maximum velocity is achieved.

The two-part construction of the inhaler allows the top housing to be changed rapidly when the supply of medicinal substance is used up or enables it to be replaced by other top housings which are filled with different medicinal substances in the strip-pull metering system.

The pump housing 37 has a rotary knob 42 which is connected to a tensioning spindle 44 and is closed off at the end face by a cover 43 provided with bores. The tensioning spindle 44, like the metering pin 8 to which it can be connected in accurate position and by torsional engagement with the coupling 32, has an axial bore 32a.

In the front part of the pump housing 37 is mounted the piston pump which can be primed and triggered. The pump has the pump piston 19 which has a pin 19b guided in a spiral groove 19d of the tensioning spindle 44. In a kinematic reversal of this principle of translatory conversion of a rotary movement, cams or the like may be provided on the tensioning spindle, these cams being accommodated in a spiral groove located in the piston bore.

In FIG. 14 the piston is in the top position after triggering and expulsion of the air, whereas FIG. 15 shows the piston in the primed state. This view shows particularly clearly the pump cylinder chamber above the piston 19 in which the air is compressed by the piston as it rises. On the pump cylinder chamber is the air outlet opening and the pressure channel 12a which opens into the bore 30 on the metering pin 8 in order to convey the dispersing compressed air into the appropriate chamber 8a or metering notch 7 (see also FIG. 11).

On the bottom of the piston is provided a radially symmetrical latching element 19c, a retaining bracket, by means of which the piston can be preloaded counter to the force of the spring 22 while engaging with an equally radially-symmetrical locking bracket 13 which has resiliently yielding segments.

The superimposed parts of the retaining and locking brackets are slightly inclined, so that the retaining bracket 19c has a tendency, under the influence of the force of the spring 22 to bring the segments of the locking brackets inwards and thereby open the lock. The inclined surface therefore assists actuation, which is also aided by the inherent tension of the segments of the locking brackets. The latching and release mechanism also has a reset button 45 which rotates with the tensioning spindle 44, and a release button 46 with a locking shoulder which is movable in the longitudinal axial direction. When the piston is primed, the release knob 46 is pressed, by means of the reset button 45 above its locking shoulder, into the locking and release brackets 13 so that the release edge of the release brackets 13 is above the locking shoulder of the release knob 46. At the same time the locking and release brackets engage in the latching element or retaining bracket 19c of the piston (FIG. 15).

The edges of the reset and release knob 45 and 46 which slide over one another with a slide member are constructed in the form of a ramp. In the primed state (FIG. 15) the highest point of the ramp has already been passed, so that the space behind the end of the ramp is available for the necessary axial movement of the release knob during actuation.

The latching means shown constitute a relatively simple solution which is also mechanically easy to assemble.

For automatic actuation of the pump during active breathing in, a particularly advantageous trigger mechanism is provided which has as its central element a membrane 47 which responds to the low pressure produced in the low pressure channel 41 and extends into the axial bore 32a, when the patient breathes in. The membrane 47 bounds the end face of a membrane chamber 48 in which is provided a membrane pot 49 on which there are actuating pins 50 which are guided in the rotary knob 42. At their other end these actuating pins abut on the release knob 46. This membrane triggering may in theory also be used for other inhalers or for mechanically triggering other technical processes.

In order to achieve the primed condition ready for inhalation shown in FIG. 15, starting from the unprimed resting condition shown in FIG. 14, the following procedures should be carried out:

the rotary knob 42 is turned manually through a certain angle. The tensioning spindle 44, the reset button 45 and the metering pin 8 rotate with the rotary knob (via the coupling 32). In the embodiment by way of example, the pitch of the spiral groove 19d is such that a 180° rotation is necessary in order to achieve the primed state.

By rotation of the rotary knob 42, the metering notch 7 is filled with the powder to be inhaled, initially by rotation of the metering pin 8 in the strip-pull metering system in the top housing 36, as has already been described in detail with reference to FIGS. 11 to 13. Moreover, rotation of the tensioning spindle 44 causes the pin 19b of the piston 19 guided in the spiral groove 19d of the tensioning Spindle to move downwards. The piston 19 thus biases the spring 22. After rotation through an angle of about 135° the piston per se is in the starting position. When the knob 42 is rotated through 45° the release button 46 is pressed into the release bracket 13 via the reset button 45 with its locking shoulder. This bracket frictionally engages in the latching element 19c of the piston.

The piston is now primed and is held in position by the locking means described above. The inclined surfaces on the locking bracket 13 and on the latching element 19c are designed so that the latching element, under the influence of the spring force, urges the locking bracket inwards in order to open the lock. However, this is prevented by the release button 46, the thicker upper part of which presses against the cams of the locking bracket and holds them in the spread-apart position. This provides a particularly advantageous protection against accidental triggering of the device.

The inhaler is now in the state of readiness as shown in FIG. 15, ie. it is ready for inhaling.

During inhalation, as the patient breathes in through the mouth piece 11, air is supplied through the foreign air opening 40. As a result of this environmental air flowing past the bore 41 and nozzle 39, an underpressure is produced in this bore 41 which is passed on through the axial bore 32a into the membrane chamber 48. The atmospheric pressure prevailing through the bores in the lid 43 forces the membrane 47 inwardly onto the membrane pot 49. The latter presses on the actuating pins 50, which in turn abut on the release button 46 and, when a certain low pressure is reached, actuate the button by causing the locking shoulder of the release button 46 to be brought over the release edge (cam) of the locking bracket 13 as a result of axial movement of this button 46. The cams of the locking brackets 13 thus enter the region of the thinner shaft of the release button and are no longer able to rest on said button. Under the influence of the inherent tension of the segments of the locking brackets, which strives to bend the spring segments inwards, and under the influence of the inwardly directed force occurring on the inclined surfaces of the locking brackets and the latching element 19c, the segments of the locking brackets bend inwardly and the frictional engagement between the brackets and the latching element 19c is undone.

These double-acting forces for release advantageously ensure particularly good reliability of actuation.

The piston 19 is moved upwards by the force of the spring 22. The jet of compressed air produced is passed through the pressure channel 12a and passes through the bore 30 into the right hand chamber 8a in the strip metering means. The powder situated in the right hand metering notch 7 is dispersed through the nozzle 29 and mixed with the respiratory flow, ie. converted into an aerosol. Then the device returns to the initial state shown in FIG. 14.

The assemblies and components used in FIGS. 14 and 15 are embodiments; however, the invention is not restricted to them. Thus, for example, other construction elements may be used for converting a rotary movement into longitudinal displacement of the piston 19 and different latching and release mechanisms can be used without departing from the invention.

FIGS. 14 and 15 illustrate a further advantage of the device according to the invention. The known inhaler described at the beginning, which is actuated in synchronism with the breathing, has a plurality of very precisely machined components which have to be combined and adjusted in a laborious assembly process. However, in the interests of cheap production of such devices it is desirable for the devices to be of very simple construction. In particular, it is necessary to assemble mass produced devices of this kind mechanically in a fast operation.

Another serious disadvantage of the known device (U.S. Pat. No. 3921637) is the fact that the breath flows through the device and over the mechanical parts. Consequently in the course of time, there will be an unavoidable deposit of dust and dirt on the precise bearing points. This may also be caused, particular, by carrying devices of this kind in pockets in clothing. flowever, any soiling of the delicate, mechanical components can interfere with the operational reliability of such devices, with possible dramatic consequences in the event of an asthma attack, for example.

Devices of the kind in question should present little resistance to the patient's breath during inhalation. This means that only slight forces are available for actuating the pulse of foreign air. Consequently, all the mechanical components should be exceptionally easy-running.

The disadvantages of known inhalers are avoided with the device according to the invention and the objectives set out are achieved. The respiratory air and the foreign air have only a very short distance to travel to the mouth piece. The foreign air flows through only the metering pin and the metering chamber beforehand. The depositing of dust and dirt is therefore avoided and the components remain easy-running. If the aerosol has to be administered urgently, eg. in the event of an acute asthma attack, the device is exceptionally simple and rapid to operate.

The parts of the structure are also relatively simple and easily assembled and therefore the device can be mass produced at favourable costs.

We claim:

1. Propellant-free inhaler comprising:

a storage chamber for containing a powdered medicinal substance to be inhaled;

a manually operable metering device connected to said storage chamber, said metering device having a metering chamber for receiving a dose of the medicinal substance;

a lateral mouth piece for active breathing in;

an air channel defined by said mouth piece for distributing the dose of medicinal substance in an air stream;

a trigger-operated pump connected to said metering chamber, said pump having a manually activated tensioning device and mechanical switching means operatively connected to said tensioning device and said air channel so that said switching means responds to a low pressure in said mouth piece produced by breathing in and actuates said tensioning device to produce a stream of foreign air which blows out the dose of medicinal substance in said metering chamber thereby dispersing the medicinal substance; and wherein said switching means includes
   a low pressure channel,
   a flexible membrane having a first and a second side, wherein the low pressure in said mouth piece extends through said low pressure channel to cause said membrane to move in response to the low pressure, said first side being exposed to the low pressure, said second side being exposed to the ambient air,
   a membrane pot disposed within a membrane chamber bounded on one side by said membrane, and
   an actuating pin.

2. Propellant-free inhaler comprising:

a storage chamber for containing a powdered medicinal substance to be inhaled;

a manually operable metering device connected to said storage chamber, said metering device having a metering chamber for receiving a dose of the medicinal substance;

a lateral mouth piece for active breathing in;

an air channel defined by said mouth piece for distributing the dose of medicinal substance in an air stream;

a trigger-operated pump connected to said metering chamber, said pump having a manually activated tensioning device and mechanical switching means operatively connected to said tensioning device and said air channel so that said switching means responds to a low pressure in said mouth piece produced by breathing in and actuates said tensioning device to produce a stream of foreign air which blows out the dose of medicinal substance in said metering chamber thereby dispersing the medicinal substance; and wherein said storage chamber comprises a magazine and said storage chamber is partially defined by a movable wall, said wall movable toward said metering device to thereby move the medicinal substance from said storage chamber into said metering chamber, wherein said movable wall includes a flexible strip having a first end and a second end, said strip being looped into said magazine to form a loop opening, the width of said magazine being limited to the width of said strip, said loop opening being closed off by a metering pin having at least one metering chamber defined by a metering notch, said first and second ends of said flexible strip traveling past and encircling said metering pin.

3. Propellant-free inhaler according to claim 2, wherein said strip comprises a flexible material having a predetermined tensile strength and surface roughness.

4. Propellant-free inhaler according to claim 2, further comprising:

a spindle;

a strip tensioning pin connected to said metering pin by a mechanical coupling; and wherein said first end of said strip is fixed to said spindle and said second end of said strip is wound onto said strip tensioning pin.

5. Propellant-free inhaler according to claim 4, wherein said mechanical coupling comprises a slip coupling which slips at a predetermined torque, thereby limiting the force with which said loop opening presses the dose of powdered medicinal substance against said metering pin.

6. Propellant-free inhaler according to claim 5, further comprising a belt which mechanically couples said metering pin to said strip tensioning pin.

7. Propellant-free inhaler according to claim 4, wherein the distance between said spindle and said strip tensioning pin is less than the diameter of said metering pin.

8. Propellant-free inhaler according to claim 2, further comprising:

a dispersing nozzle disposed downstream of said metering chamber through which the stream of foreign air is guided.

9. Propellant-free inhaler according to claim 8, wherein said dispersing nozzle is disposed in said magazine so that when said metering pin is rotated to align said metering notch with a nozzle opening in said dispersing nozzle, said dispersing nozzle is lifted away from said metering pin.

10. Propellant-free inhaler according to claim 9, wherein said magazine comprises:

two disks forming end walls of said magazine, separated by the width of said flexible strip, said metering pin being centrally mounted through said discs, said dispersing nozzle disposed between said two disks; and a spindle and a strip tensioning pin disposed between said two disks so that the inner circumferential spacing between said spindle and said strip tensioning pin is less than the diameter of said metering pin.

* * * * *